United States Patent [19]

Maltais et al.

[11] Patent Number: 5,603,902
[45] Date of Patent: Feb. 18, 1997

[54] METHOD AND APPARATUS FOR CLEANING A DIALYSATE CIRCUIT DOWNSTREAM OF A DIALYZER

[75] Inventors: Jo-Ann B. Maltais, Morrison, Colo.; Archie T. Wood, Toronto, Ohio; Roy S. Hovland, Denver, Colo.

[73] Assignee: COBE Laboratories, Inc., Lakewood, Colo.

[21] Appl. No.: 454,951

[22] Filed: May 31, 1995

Related U.S. Application Data

[63] Continuation of Ser. No. 372,112, Jan. 13, 1995, which is a continuation-in-part of Ser. No. 92,705, Jul. 16, 1993, Pat. No. 5,409,612.

[51] Int. Cl.⁶ .................... A61L 2/26; B08B 9/06
[52] U.S. Cl. ................. 422/103; 134/166 C; 134/169 C; 137/240; 210/636; 210/646
[58] Field of Search .................. 210/85, 87, 91, 210/94, 143, 136, 636, 645, 646, 321.69; 604/4; 422/28, 116, 117; 134/22.1, 22.11, 22.12, 22.13, 22.14, 104.1, 166 C, 168 C; 137/240, 238, 511, 512

[56] References Cited

U.S. PATENT DOCUMENTS

| | | | |
|---|---|---|---|
| 1,240,977 | 9/1917 | Horn | 137/240 |
| 2,098,525 | 11/1937 | Smith | 15/104.05 |
| 3,537,897 | 11/1970 | Kington . | |
| 4,153,554 | 5/1979 | van der Heide et al. . | |
| 4,158,034 | 6/1979 | Riede et al. | 422/36 |
| 4,166,031 | 8/1979 | Hardy . | |
| 4,371,385 | 2/1983 | Johnson . | |
| 4,485,840 | 12/1984 | Erwin | 137/240 |
| 4,683,053 | 7/1987 | Polaschegg | 210/86 |
| 4,702,829 | 10/1987 | Polaschegg et al. | 210/195.2 |
| 4,789,467 | 12/1988 | Lindsay et al. | 210/103 |
| 4,857,181 | 8/1989 | Shouldice et al. | 210/87 |
| 5,078,967 | 1/1992 | Riera-Aixala | 422/37 |
| 5,147,613 | 9/1992 | Heilmann et al. | 422/116 |
| 5,173,125 | 12/1992 | Felding | 134/22.11 |
| 5,256,371 | 10/1993 | Pippert | 422/28 |
| 5,421,813 | 6/1995 | Ohnishi | 604/4 |
| 5,465,875 | 11/1995 | Garnett | 137/240 |

FOREIGN PATENT DOCUMENTS 2251433  7/1992  United Kingdom .

OTHER PUBLICATIONS

COBE Centrysystem™ 3 Dialysis Control Unit Operator's Manual (1992).
COBE Centrysystem™ 3 Disinfection and Cleaning Options (1993).
Fresenius Citrosteril® brochure obtained by J. Maltais in 1992.

Primary Examiner—Joseph W. Drodge
Attorney, Agent, or Firm—Edna M. O'Connor; Bruce R. Winsor

[57] ABSTRACT

A method and apparatus for cleaning of a dialysate circuit located downstream of the dialyzer in a dialysis machine is described. The method comprises injecting a cleaning agent into the dialysis machine at a point between the dialyzer inlet port and the downstream dialysate circuit in an amount sufficient to substantially reduce the deposit in said downstream dialysate circuit; permitting flow of the agent towards the downstream dialysate circuit; and substantially preventing flow of the agent toward the dialyzer inlet port. The injection adaptor apparatus comprises an injection connector downstream of a backflow prevention valve, and two flanking tubing connectors. The apparatus is inserted at a point downstream of the dialyzer inlet port, and cleaning agent is injected into the injection connector. An adaptor to facilitate handling of cleaning agent during manual agent injection is also described. Additionally, an automated agent injection apparatus is described.

19 Claims, 4 Drawing Sheets

METHOD AND APPARATUS FOR CLEANING A DIALYSATE CIRCUIT DOWNSTREAM OF A DIALYZER

RELATEDNESS OF THE APPLICATION

This application is a continuation of copending U.S. application Ser. No. 08/372,112, filed Jan. 13, 1995, which is a continuation-in-part of U.S. application Ser. No. 08/092,705, filed Jul. 16, 1993, which issued as U.S. Pat. No. 5,409,612 on Apr. 25, 1995.

FIELD OF THE INVENTION

The invention relates to an apparatus and a method for the cleaning of dialysate waste lines, including sensors and other components disposed therein, located downstream of the dialyzer in a dialysis control machine.

BACKGROUND OF THE INVENTION

A dialysis machine or control unit comprises a dialyzer, dialysate delivery and waste systems, and blood delivery and return systems. It also can contain means for controlling and detecting pH, conductivity, temperature, and pressure of blood and/or dialysate. Such means may be located upstream or downstream of the dialyzer or both. Examples of sensors include pH, dissolved oxygen, flow switch, temperature, pressure, and conductivity sensors, and optical sensors such as a blood leak detector. Sensors located downstream of the dialyzer are typically, but not exclusively, pressure, flow switch, conductivity and blood leak detectors. As with other components of the downstream dialysate circuit, such downstream sensors can become fouled by the accumulation thereon of proteins and other organic and inorganic matter, which can impair their function and/or cause them to generate false readings. Sensors downstream of the dialyzer are more likely to acquire deposits, due to the relatively higher concentration of proteins and other organics in the spent dialysate. For example, blood leak detectors that are optical sensors, e.g., absorbance or diffraction sensors, when sufficiently fouled, can give false blood leak indications. The resulting halt in the dialysis procedure requires that the operator determine the cause of the alarm and clean the fouled blood leak detector.

Sensors can be cleaned by routine maintenance procedures, such as those described in Johnson, U.S. Pat. No. 4,371,385 (1983). Johnson describes, in columns 9 and 10, bleach and formaldehyde rinses to clean and disinfect the dialysate delivery and waste systems. In addition, the COBE Centrysystem™ 3 Dialysis Control Unit Operator's Manual (1992) describes maintenance procedures which include vinegar or acid rinse to control precipitate and bleach (sodium hypochorite) rinse to control organics. Further, the COBE Centrysystem™ 3 Disinfection and Cleaning Options (1993) manual describes cleaning procedures such as disinfection with Actril™, Renalin™ and formaldehyde solutions, and organics control with bleach or TERG-A-ZYME™. As discussed in detail hereinbelow, each of the Johnson and COBE procedures involve cleaning both the dialysate delivery and waste systems. No procedure is provided specifically for the cleaning of sensors downstream of the dialyzer. Routine maintenance procedures that involve both the dialysate delivery and waste systems may not be adequate to clean the more heavily contaminated downstream sensors. Moreover, using the routine procedures on an as-needed basis to correct contaminated downstream sensors can be time-consuming. For example, for a routine bleach cleaning, the procedure can require at least 20 minutes. This can disrupt scheduled machine use.

A downstream sensor can also be cleaned by disassembly of the contaminated sensor, manual removal of the contamination, and reassembly of the sensor. For example, von der Heide et al., U.S. Pat. No. 4,153,554 (1979), describe such a method for a fouled blood leak detector. The detector is described as a photocell with two glass windows. The detector can give false readings of a blood leak in the spent dialysate if the window(s) of the photocell acquire a "film," which interferes with the passage of light. At column 8, lines 30–35, it is stated that this situation can be remedied by chemically removing the films from the windows of the photocell by "physically opening the blood leak detector by removing the top . . . which is held in place by screws . . . , and cleaning the windows . . . through the open top of [the] screen . . . " of the detector. To temporarily avoid disassembly of the dialyzer apparatus and avoid a false reading of the blood detector, von der Heide et al. suggest attenuating the sensitivity of the blood detector by adjusting the blood leak sensitivity limit. The suggestion of van der Heide et al. that an alternative method be used to temporarily avoid disassembly reflects the inconvenience and delay associated with sensor disassembly, cleaning and reassembly.

Therefore, there is a clear need for a rapid, simple procedure for cleaning sensors located downstream from the dialyzer. Preferably, the procedure requires significantly less time than that required for routine or maintenance cleaning procedures, so that disruption of scheduled machine use is minimized. Also, the procedure must be sufficiently rigorous to remove substantially all of the deposits on the components of the downstream dialysate circuit, but must not present a hazard to the next dialysis patient.

SUMMARY OF THE INVENTION

The subject invention is a method and apparatus for reducing contamination in the dialysate circuit downstream of the dialyzer in a dialysis machine. The method comprises injecting a cleaning agent at a point downstream of the inlet port of membrane fluid treatment devices, such as a dialyzer, in an amount sufficient to substantially reduce the deposits in the downstream dialysate circuit; permitting flow of the agent towards the downstream dialysate circuit; and substantially preventing flow of the agent toward the dialyzer. Membrane fluid treatment devices, include, but are not limited to, blood dialyzers and hemodiafiltration dialyzers, such as are described in Polaschegg et al. (1987) U.S. Pat. No. 4,702,829. As discussed hereinbelow, "downstream of the inlet port of a membrane fluid treatment device" means in the case of a blood dialyzer, downstream of the blood dialyzer inlet connector connected to the dialysate supply line when the dialysate supply line has been disconnected from the blood dialyzer and connected to a bypass block. In the case of a hemodiafiltration dialyzer, "downstream of the inlet port of a membrane fluid treatment device" means downstream of the hemodiafiltration dialyzer inlet connector connected to the dialysate supply line; typically, the point of injection is downstream of the hemodiafiltration dialyzer outlet connector. As is known in the art, dialyzer membranes can be damaged by cleaning agents; thus, the agent is injected so as to bypass the dialyzers.

The subject method has the advantage of having the capacity to be performed either while the patient's blood is connected to or disconnected from the dialyzer. During the procedure, the dialysate supply and return lines are disconnected from the dialyzer and connected to the bypass block. If the patient's blood remains connected during the cleaning procedure, it continues to recirculate via a blood pump and an extracorporeal circuit which is a closed circuit due to disconnection of the patient's venous and arterial blood lines from the blood supply and return lines in fluid communication with the dialyzer. The patient's arterial and venous lines are typically connected to each other via a sterile connector and may be clamped. Because the subject method requires significantly less time than prior art cleaning methods, it is possible to keep the patient's blood recirculating during the cleaning procedure without encountering significant problems with blood clotting in the dialyzer or blood supply and return lines.

The cleaning agent can be an enzyme, detergent, oxidizer, corrosive, solvent, or any combination thereof, of alkaline, acidic or neutral pH. Following injection of the agent, the downstream dialysate circuit is then thoroughly rinsed with a rinse fluid such as water or dialysate to remove substantially all of the agent. Typically, dialysate can be used as the rinsing agent when the patient's blood remains connected to the dialyzer, while water can be used when the cleaning procedure is done with the patient's blood disconnected, e.g., between patients or when a patient has been disconnected after a blood leak indication.

The injection adaptor apparatus of the subject invention comprises a first tubing connector; a backflow prevention valve in fluid communication with the first tubing connector; an injection connector in fluid communication with the backflow prevention valve; and a second tubing connector in fluid communication with the injection connector. The backflow prevention valve is oriented to allow flow only in a direction from the first connector to the second connector. Using the tubing connectors, the apparatus is inserted in the dialysis machine at a point downstream of the dialyzer inlet port and upstream of the region of the downstream dialysate circuit to be cleaned. Backflow into the dialyzer or to points upstream of the dialyzer is substantially prevented by using a backflow prevention valve, such as a check valve.

The region of the downstream dialysate circuit to be cleaned typically has sensors disposed therein. Downstream sensors include, but are not limited to, pH, dissolved oxygen, blood leak, temperature, and pressure sensors.

The injection connector can be, for example, a tee connector or an injection port. Where the connector is an injection port, a syringe or a needle and syringe with cleaning agent can be used to inject agent into the port. In another embodiment, the injection procedure is facilitated by using an agent container adaptor, which allows loading of the syringe directly from the container comprising the cleaning agent. The container adaptor comprises a tube that can be secured at one end to the container opening and secured at the other end to the syringe, thereby providing fluid communication between the container and adaptor and the adaptor and the syringe. The syringe is then loaded with the agent by withdrawing the plunger. Once loaded, the syringe is disengaged from the end of the adaptor. Depending on whether the injection port comprises a septum, luer connector or other connector, the loaded agent can then be injected into the injection port directly from the syringe, or a needle or other facilitating device can be attached to the syringe to engage the injection port flow path. If a needle is used, it can be a sharp or blunt end needle, depending on the nature of the injection port. In any embodiment employing the injection port, it is preferred that the injection adaptor apparatus be inserted at the point between the external spent dialysate line and its bypass block connector, as described hereinbelow.

Where the injection connector is a tee connector, injection can be accomplished by an automated agent injection apparatus, which comprises a tubing which has a first end and a second end; with the first end of the tubing secured to the opening of the cleaning agent container, whereby the tubing and the container are in fluid communication; and with the second end of the tubing secured to the injection tee connector to provide fluid communication with the tee connector. In this embodiment, it is preferred that the tee connector be located within the bypass block of the dialysis machine. Agent is then pumped from the container through the tubing into the tee connector. A backflow prevention valve in the bypass block upstream of the tee connector substantially prevents backflow of the agent to a point upstream of or into the dialyzer. A backflow prevention valve in the agent tubing, located either downstream of or incorporated into the pump, prevents backflow of the agent in the tubing and prevents excessive dilution of agent by dialysate.

The subject apparatus and method have the advantage of providing an intensive cleaning of sensors downstream of the dialyzer, while substantially preventing exposure of the next dialysis patient to the agent. The next patient is not exposed to the agent because, during the cleaning procedure, the blood dialyzer is disconnected from the external dialysate delivery and waste lines, the external dialysate delivery and waste lines are connected to their respective connectors of the bypass block, and the point of injection is downstream of the dialysate supply line blood dialyzer inlet connector or downstream of the hemodiafiltration dialyzer inlet port, with a backflow prevention valve upstream of the injection site.

An additional advantage is that the subject method can be completed in substantially less time than methods employing sensor disassembly, cleaning and reassembly. The subject method can also be completed in substantially less time than routine or maintenance rinses which involve both the dialysate delivery and waste systems. Thus, disruption of scheduled machine use is minimized. Additionally, the subject method requires less cleaning agent. Further, the subject method provides for intensive cleaning of the downstream dialysate circuit without exposure of dialyzer membranes to cleaning agents, such as bleach, which could damage the membrane.

DETAILED DESCRIPTION OF THE INVENTION

The presently preferred embodiments of the invention will now be described with reference to the drawings. The presently preferred embodiments will also be described with reference to the COBE Centrysystem™ 3 Dialysis Control Unit, but it will be appreciated by those having skill in the art that the present invention is applicable to any dialysis control unit incorporating sensors downstream of a dialyzer.

Figure 1:
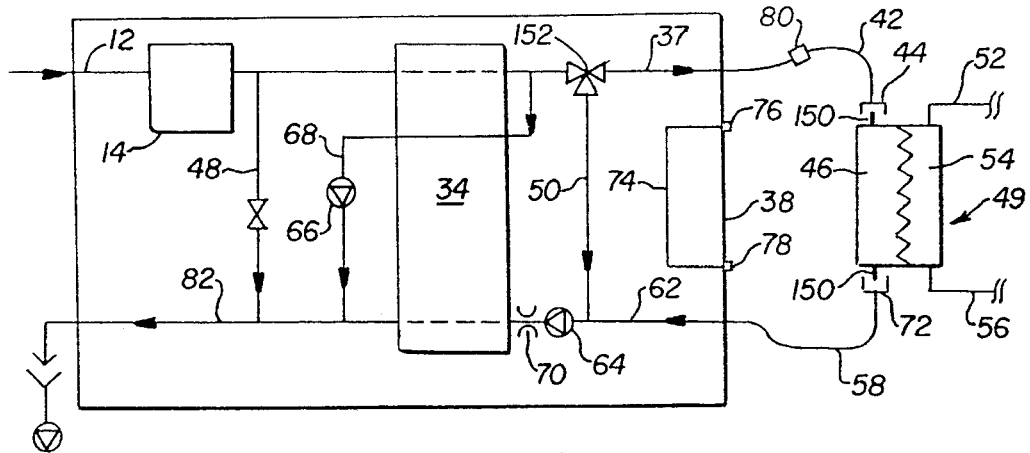
FIG. 1 is a simplified schematic illustration of a single pass dialysis control unit and dialyzer during a dialysis procedure as is known in the prior art.

FIG. 1 is a simplified schematic diagram of the COBE Centrysystem™ 3 dialysis machine 10 during dialysis. Certain details of the Centrysystem™ 3 not related to the present invention have been omitted for clarity. Water enters line 12 and is conducted through several steps summarily represented as dialysate preparation apparatus 14, and which can include addition of bicarbonate and acid, or acetate. The resulting dialysate is then conducted to the ultrafiltration control (UFC) circuit 34. The UFC circuit ensure that the dialysate volume into the dialyzer is equal to the spent dialysate out. The dialysate then is transported through internal dialysate supply line 37, through the surface of the front panel 38 into external dialysate line 42, through dialysate line dialyzer inlet connector 44, and into the dialysate portion 46 of the dialyzer 49. If desired, dialysate can be directed through dump line 48 or through bypass line 50. During dialysis, blood is pumped from the patient through blood supply line 52 into the blood portion 54 of the dialyzer 49, and then back to the patient through return line 56. The spent dialysate leaves the dialyzer 49 to the external spent dialysate line 58 through the Hansen™ connector 72, then transits the front panel 38 into internal spent dialysate line 62. Pump 64 conveys the spent dialysate through the UFC circuit 34 to drain line 82. Ultrafiltrate is pumped from the internal dialysate supply line 37 by ultrafiltrate pump 66 through line 68 to drain line 82. Blood detector 70, disposed in the spent dialysate line 62, is an optical sensor that measures hemoglobin. The spent dialysate is next conveyed through UFC circuit 34 to drain line 82, and then to a drain for disposal. During dialysis, the bypass block 74 is not in use. An apparatus controller (not shown) may be provided to automatically control all or a portion of the dialysis control unit operations.

Figure 2:
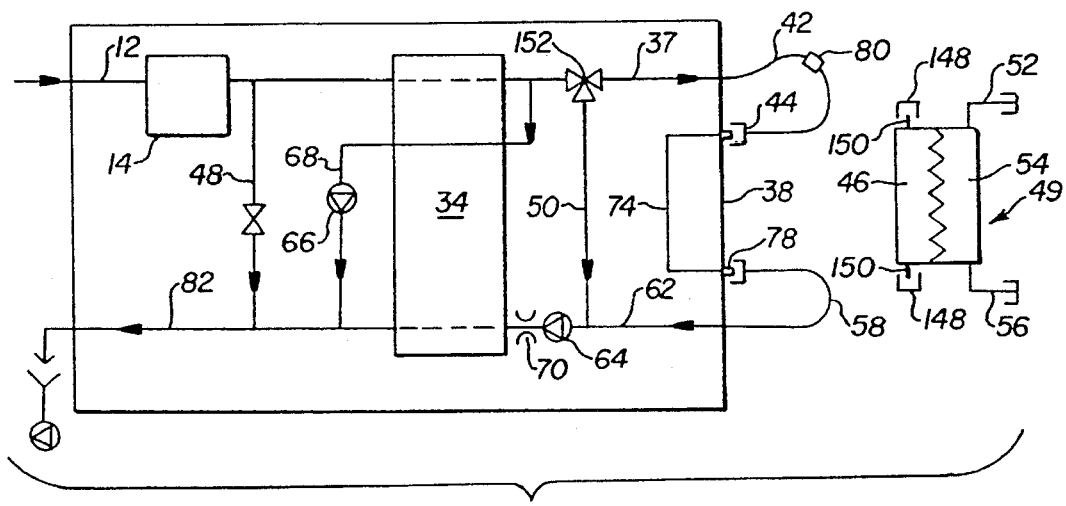
FIG. 2 is a simplified schematic illustration of a single pass dialysis control unit and dialyzer with the dialyzer disconnected as for a cleaning procedure, as is known in the prior art.

FIG. 2 illustrates the dialysate flow during prior art cleaning procedures. Such cleaning procedures have been undertaken as a matter of scheduled maintenance or when a false blood leak indication has occurred. A false blood leak is evident if a blood leak warning or alarm occurs without an attendant blood leak. Following the blood leak alarm, dialysis is automatically ceased. To determine if a blood leak has actually occurred after either a warning or alarm, the spent dialysate exiting from spent dialysate line 82 is first examined for pink or red color, and with a Hemastix™ test strip which can detect approximately 0.15 mg of hemoglobin per liter of dialysate. Failure to detect blood in the spent dialysate line 82 can indicate a false blood leak alarm or warning due to a fouled blood leak detector 70.

In the prior art cleaning procedure, the patient is completely disconnected from the dialyzer, i.e., there is not extracorporeal recirculation of the patient's blood. Bleach (e.g., sodium hypochlorite) from container 124 or other cleaning solution is conveyed to an addition unit that is a component of dialysate preparation apparatus 14. During the cleaning procedure, external dialysate lines 42 and 58 are connected to male Hansen™ connectors 76 and 78, respectively, creating a continuous flow path from external supply dialysate line 42, to bypass block 74, and external spent dialysate line 58. Thus, the cleaning agent solution flows through at least a portion of the dialysate preparation apparatus 14, through UFC circuit 34, into a portion of the ultrafiltrate line 68 and pump 66, through external dialysate supply line 42, through bypass block 74 to external spent dialysate line 58, into internal spent dialysate line 62, through pump 64 past the blood detector 70, into UFC circuit 34, then through line 82 to the drain. Following the agent cleaning procedure, all components that came in contact with the agent must be thoroughly rinsed. Rinsing must continue until samples from the drain line 82 and predialyzer sample port 80 located in the external dialysate line 42 have less than 0.5 ppm free chlorine, in the case of the bleach cleaning procedure. The bleach cleaning and rinsing procedure has been observed to require at least 20 minutes.

In contrast to the prior art, the subject inventive method is specifically directed to cleaning sensors downstream of the external dialysate line dialyzer inlet connector 44. In one embodiment, the cleaning agent is injected into an injection connector inserted between the external spent dialysate line 58 and its bypass block connector 78. In another embodiment, cleaning agent is injected in the bypass block 74. In both embodiments, the length of the pathway for the cleaning agent and the water rinse is about half or less than half the cleaning agent pathway in the prior art. Thus, the subject method requires substantially less cleaning agent and substantially less time to selectively and more effectively clean the downstream detector 70 or other downstream sensors. It has been found that a 20 cc sodium hypochlorite rinse followed by a water rinse can require about 5 minutes. Insertion of the injection apparatus into the dialysis machine, loading of the syringe, injection of the bleach and rinsing with water can require about 10 minutes.

Figure 3:
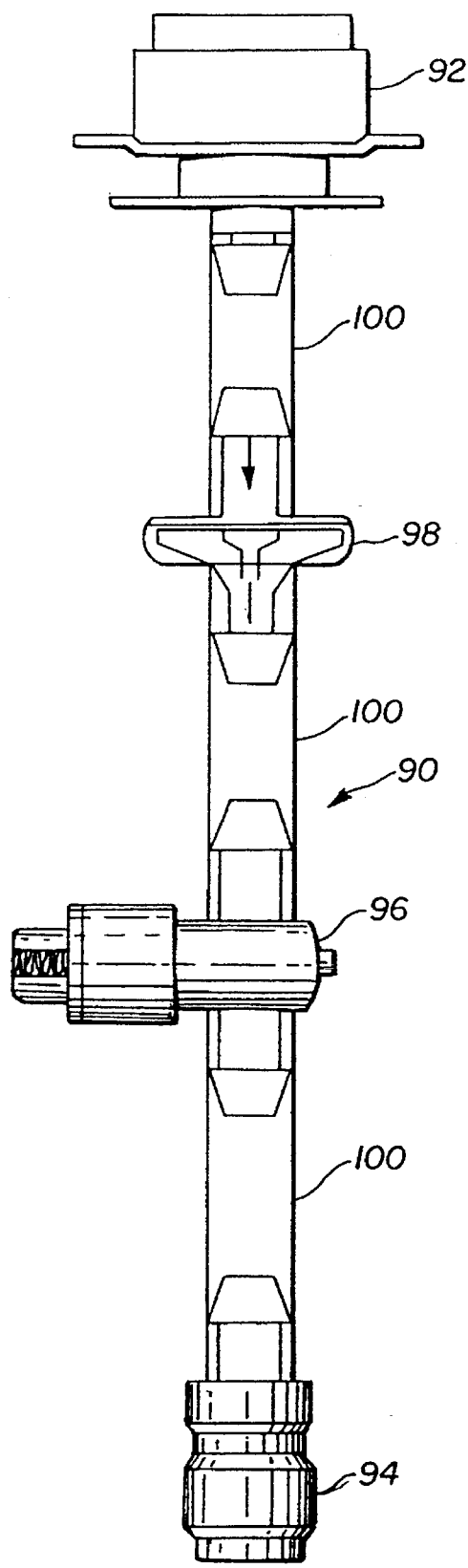
FIG. 3 illustrates the cleaning agent injection adaptor.
Figure 4:
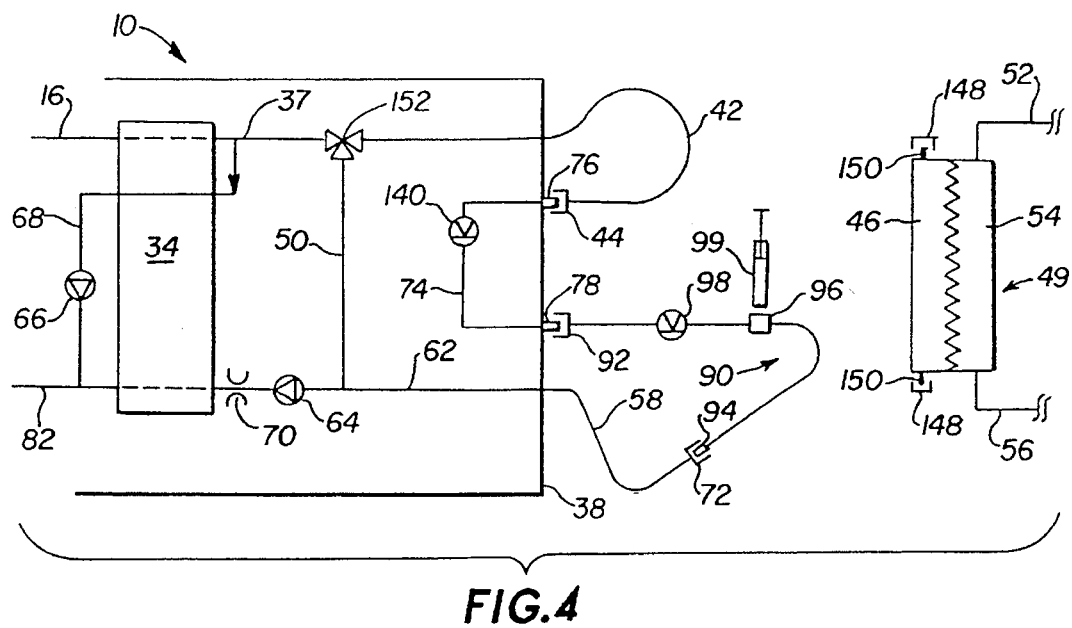
FIG. 4 is a schematic illustration of a preferred location in a single pass dialysis machine for insertion of the injection adaptor apparatus of FIG. 3.

In the first embodiment, an injection adaptor 90, as illustrated in FIG. 3, is inserted between the bypass block 74 and the external spent dialysate line 58. Injection adaptor apparatus 90 comprises connectors 92, 94 at either end, injection port 96, at least one backflow prevention valve 98, and tubing segments 100 to bring the foregoing components into fluid communication. The tubing segments 100 are typically 2–3 inches in length and are made of appropriate material such as silicone. As illustrated in FIG. 4, it is preferred that the upstream connector 92 be a female Hansen™ adaptor compatible with the bypass block male connector 78, and that the downstream connector 94 be a male Hansen™ adaptor compatible with the female Hansen™ connector 72 of external spent dialysate line 58. Male Hansen™ adaptor may have a flange. The backflow prevention valve 98, located upstream of the injection port 96, substantially prevents flow of cleaning agent to a point upstream of external dialysate line's inlet connector 44. In this arrangement, the injected agent flows through tubing segment 100 and connector 94 into the external spent dialysate line 58, through the front panel 38 into internal spent dialysate line 62, where it makes contact with the blood leak detector 70. The agent is next conveyed by pump 64 through UFC circuit 34 to drain line 82.

As discussed above, upon occurrence of a blood leak alarm event, the operator must determine if the alarm is the result of a blood leak or of fouling of the detector 70. If the spent dialysate is pink or red in color or if a Hemastix™ test strip indicates the presence of blood, dialysis should be ceased. If the presence of blood is not verified, the blood leak detector is fouled and must be cleaned.

An exemplary procedure for the cleaning procedure illustrated in FIG. 4 will be described by reference to the COBE Centrysystem™ 3 Dialysis Control Unit. Skilled artisans will recognize that variations in the procedure are possible for use in conjunction with the COBE Centrysystem™ 3 and other dialysis control units. Following the occurrence of a blood leak alarm with no attendant blood leak, or at a regularly scheduled bleach cleaning, the operator, in the case of the COBE Centrysystem™ 3, sets the machine in Rinseback or Set-Up mode for the bleach cleaning procedure. The operator initiates the bleach or cleaning agent procedure by inputting an appropriate command into the apparatus controller (not shown), which is typically a microprocessor, which places the dialysis apparatus in a bypass mode. In the bypass mode, a bypass valve 152 disposed in line 37 directs the flow of clean dialysate directly to the spent dialysate line 62, rather than routing it through the dialyzer 49. External spent dialysate line 58 and external dialysate supply line 42 are then disconnected from the dialyzer 49, and caps 148 are placed on the dialyzer dialysate ports 150. The patient's blood is recirculated as a closed circuit via the blood tubing set 52, 56 and a blood pump (not shown). The external dialysate supply line 42 is then connected to its bypass block connector 76. The injection adaptor apparatus 90 is inserted between the bypass block 74 and external spent dialysate line 58, by connecting female Hansen™ connector 92 of injection apparatus 90 with male Hansen™ connector 78 of the bypass block, and by connecting female Hansen™ connector 72 of the external spent dialysate line 58 with male Hansen™ connector 94 of the injection apparatus 90. The operator then initiates a bleach cleaning procedure by entering an appropriate command into the apparatus controller (not shown), which causes switches or sensors (not shown), such as conventional limit switches, to send a signal to the apparatus controller (not shown) that verifies that female Hansen™ connector 44 of the external dialysate supply line 42 and female connector 92 of injection adaptor apparatus 90 are properly connected to bypass block connectors 76 and 78, respectively. If the proper connection has been made, the apparatus controller takes the dialysis control unit 10 out of the bypass mode, causing the bypass valve 152 to redirect dialysate through external dialysate supply line 42, the bypass block 74, the injection adaptor apparatus 90, the external spent dialysate line 58, the internal spent dialysate line 62, the UFC circuit 34, and drain line 82. The operator should then check, via a pressure sensor (not shown), the dialysate pressure to assure that it is less than atmospheric prior to injecting bleach into the injection adaptor apparatus. To reduce the dialysate pressure, the apparatus controller can also increase the rate of ultrafiltrate pump 66, resulting in an increase in ultrafiltration rate, and a reduced pressure in the injection adaptor apparatus 90. The operator then injects bleach (typically about 20 cc) into the injection port 96 using a syringe 99 loaded with bleach. Alternatively, a syringe 99 with a needle can be used. If the operator notices resistance while injecting the bleach, he can withdraw about 20 cc of fluid from the injection port 96 and again attempt bleach injection. Backflow prevention valve 140 substantially prevents backflow of the agent to a point upstream of the dialyzer. Backflow prevention valve 140 comprises at least one check valve. It may be desirable to verify the functioning of backflow prevention valve(s) 140 at the beginning of each cleaning procedure by observing the direction of flow of cleaning agent in the bypass block 74 following injection of cleaning agent. After completing the bleach injection, the operator may visually verify that the deposits are no longer visible. If deposits are still present, the bleach injection can be repeated. Dialysate is then run through the dialysis control unit 10 for a period sufficient to rinse substantially all the bleach from injection adaptor apparatus 90, from external and internal spent dialysis lines 58 and 62, and blood leak detector 70. Typically, and to reduce the time required for rinsing, the dialysate is run through the dialysis control unit 10 for a period of one minute after cleaning agent injection; then, after putting the dialysis control unit 10 in bypass mode, the injection apparatus adaptor 90 is removed from the dialysis unit 10, the external spent dialysate line 58 is reconnected to its bypass block connector 78, and the dialysis control unit 10 is removed from bypass mode to permit rinsing of the bypass block 74, and the external and internal dialysate waste lines 58 and 62 for an additional 3–4 minutes. Since the Centrysystem™ 3 is in Rinseback or Set-Up mode, the dialysis control unit 10 must first be removed from the Set-Up or Rinseback mode to the Ready mode and then Set-Up must be reinitiated, in order for the apparatus controller (not shown) to recalibrate the blood leak detector 70. The flow of dialysate is then stopped or bypassed, the operator removes caps 148 from the dialyzer dialysate ports 150, and the external dialysate lines 42 and 58 are reconnected to their dialyzer dialysate ports 150. If desired, dialysis can then be resumed.

Figure 5:
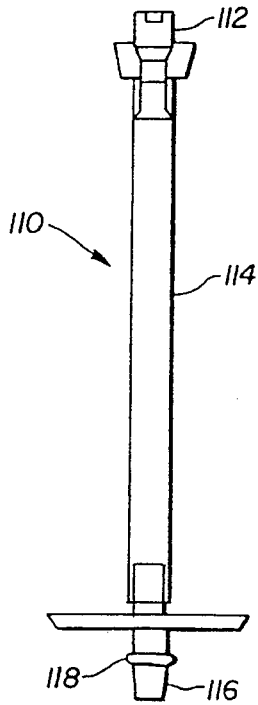
FIG. 5 illustrates the cleaning agent container adaptor.
Figure 6:
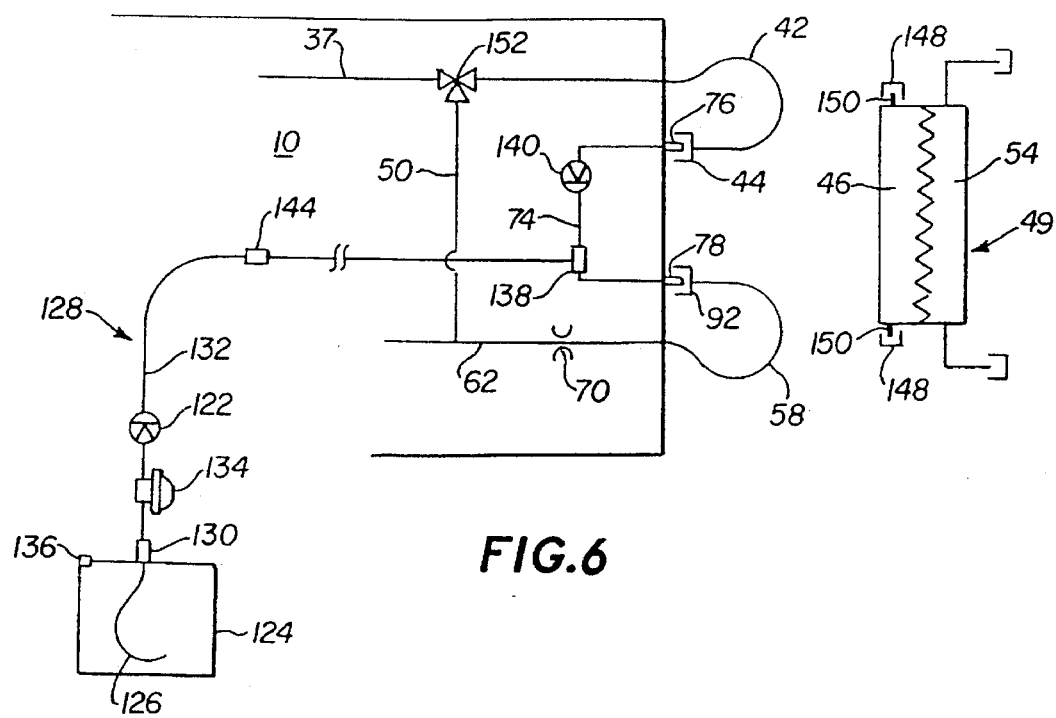
FIG. 6 illustrates an automated system for delivery of cleaning agent to an injection connector located in the bypass block of a single pass dialysis machine.

FIG. 5 illustrates a preferred embodiment of the cleaning agent container adaptor apparatus 110, which is useful with the injection adaptor apparatus 90. A connector 112, preferably a luer lock connector, allows mating with a syringe 99 (FIG. 4). The tubing 114 can be of any suitable composition that is compatible with the cleaning agent. For example, for sodium hypochlorite, Tygon™ tubing is suitable. The connector 116 allows mating with the opening of the cleaning agent container (not shown). As shown in FIG. 6, the opening of the cleaning agent container 124 can be in fluid communication with an internal tube 126 which is in contact with the agent. The end of tube 126 in contact with the agent can be notched or otherwise modified to prevent the tube from becoming flush with interior container walls. In the case of a bleach container, the connector 116 of the container adaptor apparatus is a male connector with an O-ring 118 that provides a seal between the apparatus 90 and the container 124. The syringe 99 is loaded with bleach by attaching the syringe 99 to the luer connector 112 on the container adaptor 110, and withdrawing bleach from the container 124 by drawing back on the syringe plunger. Air trapped in the syringe 99 is removed by repeated pushing and pulling on the syringe plunger until bleach substantially fills the syringe 99. Vacuum in the container 124 is relieved by a small vent hole 136 (FIG. 6) in the top of the container.

FIG. 6 illustrates the automated injection apparatus 128. Cleaning agent container 124 is in fluid communication with connector 130, which in turn is in fluid communication with agent tubing 132. Connector 130 can be a male connector with an O-ring to provide a seal with the opening of the cleaning agent container 124. Volumetric pump 134 withdraws agent from the container 124 through line 132. Vacuum within the container 124 is relieved by air inlet or vacuum release valve 136. As discussed above, container 124 can contain an internal tube 126 that is in contact with the agent, and in fluid communication with the container opening. Line 132 conducts agent to the injection tee connector 138 located in bypass block 74, which is downstream of the external dialysate line's dialyzer female Hansen™ inlet connector 44. Backflow prevention valve 122 located downstream of or incorporated into pump 134 substantially prevents backflow of agent to the container and prevents excessive dilution of the agent bolus with the dialysate. Backflow prevention valve 140 substantially prevents backflow of the agent to a point upstream of the dialyzer. Backflow prevention valve 140 comprises at least one check valve. It may be desirable to verify the functioning of check valve(s) 140 at the beginning of each cleaning procedure by observing the direction of flow of cleaning agent in the bypass block 74 following injection of cleaning agent.

Optional flow sensor 144 detects the existence and rate of flow in line 132. The flow of agent in the line 132 is communicated from sensor 144 to the front panel, to provide appropriate indications to the operator in the event that agent is flowing when it should not be or is not flowing when it should be.

Pump 134 can be any suitable pump, such as a positive displacement pump (e.g., peristaltic, diaphragm or piston). The flow rate in line 132, as determined by the pump, is controlled by any conventional pump flow rate control techniques, such as controlling pump speed from an apparatus controller (not shown), that are well known in the art.

An exemplary procedure for automatic bleach cleaning procedure will be described by reference to the COBE Centrysystem™ 3 Dialysis Control Unit. It will be appreciated by those having skill in the art that many variations of this control procedure are possible for use in conjunction with the COBE Centrysystem™ 3 and other dialysis control units. As discussed above, the need for a bleach cleaning of the blood leak detector 70 is recognized by the operator either because of the occurrence of a blood leak alarm with no attendant blood leak, or because a regularly scheduled bleach cleaning is due. The operator initiates the bleach cleaning procedure by inputting an appropriate command into the apparatus controller (not shown). The apparatus controller (not shown) places the dialysis apparatus in a bypass mode. In the bypass mode a bypass valve 152 in the dialysis apparatus directs the flow of clean dialysate directly to the spent dialysate line 62 rather than route it through the dialyzer. The operator then disconnects the external spent dialysate line 58 and the external dialysate supply line 42 from the dialyzer 49, places caps 148 on the dialyzer dialysate ports 150 of the dialyzer 49, and connects the two external dialyzer lines 42, 58 to their respective connectors 76, 78 of the bypass block 74. The operator then initiates a bleach cleaning procedure by entering an appropriate command into the apparatus controller (not shown). Switches or sensors (not shown), such as conventional limit switches, generate a signal which is sent to the apparatus controller (not shown) to verify that the dialyzer lines 42, 58 are properly connected to the bypass block connectors 76, 78. If the hoses 42, 58 are properly connected to the bypass block connectors 76, 78, the apparatus controller takes the dialysis control unit 10 out of the bypass mode, causing the bypass valve 152 to redirect the flow of dialysate through the external dialysate supply line 42, the bypass block 74, the external spent dialysate line 58, the internal spent dialysate line 62, and the blood leak detector 70, and out of the unit as spent dialysate. The apparatus controller (not shown) actuates the bleach uptake pump 134 to deliver a prescribed volume of bleach at a prescribed rate. The apparatus controller (not shown) may also increase the rate of the ultrafiltrate pump 66 to create a slightly negative pressure in the bypass block relative to atmospheric pressure, so as to facilitate injection of the bleach. If the flow sensor 144 does not detect positive flow from the bleach container 124 to the injection site 138, the apparatus controller actuates an alarm indicative of an empty bleach container 124 and suspends the bleach cleaning procedure. After the bleach cleaning, clean dialysate is run through the dialysis control unit 10 for a time sufficient to rinse the bleach from the bypass block 74, from external and internal spent dialysate hoses 58 and 62, and blood leak detector 70. The blood leak detector 70 can then be calibrated by the apparatus controller (not shown). The flow of dialysate may then be stopped or bypassed and the external dialyzer lines 42, 58 may then be disconnected from the bypass block connectors 76, 78, the caps 148 removed from the dialyzer dialysate ports 150, and the external dialyzer lines 42, 58 reconnected to the dialyzer dialysate ports 150. Dialysis may be resumed, if appropriate.

In an alternative embodiment of the automatic cleaning apparatus and procedure of the present invention, the UFC circuit 34 may be implemented as two flow meters, one in each one of the dialysate supply line 37 and the dialysate waste line 62, such as is done in the FCM-10-2™ ultrafiltration control module of the GAMBRO AK-10™ dialysis control unit, for example. In the FCM-10-2™ module the flow meters are calibrated by periodically placing the flow meters in series to ensure that substantially identical fluid flows pass through both meters during calibration, in the fashion described in U.S. Pat. No. 4,585,552 to Gummesson et al., which is incorporated herein in its entirety by reference. The comparisons and adjustments necessary for calibration may be performed by the apparatus controller. The operation of the automatic cleaning apparatus and procedure may be coordinated with the flow meter calibration so that a cleaning procedure occurs simultaneously with the flow meter calibration, or it may incidentally occur during certain flow meter calibration and not others. In either of these cases, when the flow meters are placed in series for calibration concurrently with a cleaning procedure, the cleaning agent flow causes the fluid flow through the two flow meters to not be substantially identical, but instead to differ by the amount of the cleaning agent flow. In that event, the apparatus controller is programmed to recognize that simultaneous calibration and cleaning are taking place and to account for the cleaning agent flow, calibrating the flow meters to flow values differing by the amount of the cleaning agent flow.

For any of the foregoing embodiments, the cleaning agent is selected on the basis of its compatibility with the dialysis machine sensors and tubing and its capacity to degrade or remove deposits in the downstream dialysate waste circuit, or more specifically, on the blood leak detector. The cleaning agent can be an enzyme, detergent, an oxidizer, corrosive, solvent or any combination thereof, of alkaline, acidic or neutral pH. For example, the agent can be an enzyme and detergent mixture such as TERG-A-ZYME™, or a bleach mixture or solution, such as aqueous hydrogen peroxide, sodium hypochlorite, sodium chlorite, hypochlorous acid, etc. Sodium hypochlorite is a preferred bleach because of its disinfectant and biofilm removal properties, and its high pH (about 11) makes it effective in removal of deposited organics. The agent can also be a solution or mixture of nitric acid or citric acid to remove inorganic materials such as carbonate precipitate. Additionally, a microbial disinfectant mixture or solution, such as peracetic acid, can be used as the agent. The cleaning agent is injected in an amount sufficient to substantially reduce the deposit on the blood leak detector. "Substantial reduction" of the deposit means removal of a sufficient quantity of deposit to improve sensor performance.

All references cited herein are incorporated by reference in their entirety.

Presently preferred embodiments of the subject invention have been described with some particularity. It should be understood that this description has been made by way of preferred examples and that the invention is defined by the scope of the following claims.

We claim:

1. An apparatus for reducing deposits in a portion of a dialysate circuit located downstream of a membrane fluid treatment device in a dialysis machine while not contaminating a portion of the dialysate circuit located upstream of the membrane fluid treatment device, said apparatus comprising:

a first tubing connector selectively connectable and disconnectable with a bypass block connector of the dialysate circuit;

a backflow prevention valve in fluid communication with the first tubing connector;

an injection connector in fluid communication with the backflow prevention valve and adapted for fluid communication with a source of fluid; and a second tubing connector selectively connectable and disconnectable with the dialysate circuit in fluid communication with the injection connector;

wherein said backflow prevention valve is oriented to allow flow only in a direction from the first connector to the second connector.

2. The apparatus of claim 1, wherein the membrane fluid treatment device is a hemodiafiltration dialyzer.

3. The apparatus of claim 1, wherein the membrane fluid treatment device is a blood dialyzer.

4. The apparatus of claim 1, wherein the injection connector is an injection port.

5. The apparatus of claim 4, further comprising:

a syringe in fluid communication with the injection port.

6. The apparatus of claim 5, wherein said fluid communication between said syringe and injection port comprises a needle.

7. The apparatus of claim 1, wherein the injection connector is a tee connector.

8. The apparatus of claim 7, further comprising:

a tubing having a first and a second end, said second end being in fluid communication with the tee connector;

a container containing a cleaning agent and comprising an opening, said opening being in fluid communication with the first end of the tubing; and a pump for pumping the agent through the tubing from the container to the injection connector.

9. The apparatus of claim 8, wherein the tubing further contains a flow sensor.

10. The apparatus of claim 8, further comprising a backflow prevention valve located in the pump or tubing.

11. The apparatus of claim 8, wherein the container further comprises:

an internal tube that is in contact with said agent and in fluid communication with the opening of the container; and an air inlet valve.

12. The apparatus of claim 8, further comprising:

a container adaptor through which the first end of the tubing communicates with the container opening.

13. The apparatus of claim 1, wherein the first tubing connector comprises a female connector and the second tubing connector comprises a male connector.

14. The apparatus of claim 1, wherein the backflow prevention valve comprises a check valve.

15. The apparatus of claim 14, wherein the backflow prevention valve comprises a plurality of check valves.

16. The apparatus of claim 1, wherein the fluid communication between the back flow prevention valve and the first tubing connector, between the injection connector and the backflow prevention valve and between the second tubing connector and the injection connector comprise silicone tubing.

17. The apparatus of claim 1, wherein a sensor is disposed in the downstream dialysate circuit.

18. The apparatus of claim 17, wherein the sensor is an optical sensor.

19. The apparatus of claim 18, wherein the sensor is a blood leak detector.

* * * * *